United States Patent [19]

Gallo

[11] 4,124,028
[45] Nov. 7, 1978

[54] ELECTROEJACULATION DEVICE

[75] Inventor: John A. Gallo, Reading, Mass.

[73] Assignee: Ideal Instruments, Inc., Chicago, Ill.

[21] Appl. No.: 784,122

[22] Filed: Apr. 4, 1977

[51] Int. Cl.² .............................................. A61N 1/38
[52] U.S. Cl. .............................. 128/407; 128/419 S; 128/422
[58] Field of Search ............... 128/407, 408, 404, 405, 128/419 R, 419 E, 419 S, 421–423, 24.1, 24.4, 24.5

[56] References Cited

U.S. PATENT DOCUMENTS

| 2,808,834 | 10/1957 | Marden | 128/419 S |
| 3,403,684 | 10/1968 | Stiebel et al. | 128/407 |
| 3,794,022 | 2/1974 | Nawracj et al. | 128/422 |
| 3,933,147 | 1/1976 | DuVall et al. | 128/408 |

FOREIGN PATENT DOCUMENTS

| 1,145,749 | 3/1969 | United Kingdom | 128/407 |
| 2,211,937 | 5/1968 | U.S.S.R. | 128/407 |

OTHER PUBLICATIONS

Furman et al., "Electroejaculation of Bulls... Length", J. Anim. Sci. 40(4); 1975.

Watson et al., "Field Collection...Electroejec.", Aust. Vet. J., 40(4), pp. 183–187, Apr. 1964.

"Transjector", Nicholson Manufacturing, Inc., (Advertisement).

"C.G.S. Electrojector", V.S. Supplies Ltd., Australien Vet. Precticioner, Jun. 1966, p. 66.

*Primary Examiner*—Lee S. Cohen
*Attorney, Agent, or Firm*—Kenway & Jenney

[57] ABSTRACT

An electroejaculation device has a hollow insulating housing with a set of longitudinally extending electrodes projecting from its outer surface. The housing encloses an electronic circuit that applies a sinusoidal output signal of alternating stimulation and rest periods to the electrodes. The circuit automatically increases the signal strength during successive stimulation periods through the cycle and varies the frequency of the signal during at least part of each stimulation period. An electrical plug sealed in one end of the housing connects the circuit to an external power source and preferably includes by-pass connections that allow the circuit to apply its output signal to the electrodes of a second probe that does not include a self-contained signal generating circuit.

21 Claims, 12 Drawing Figures

ELECTROEJACULATION DEVICE

BACKGROUND OF THE INVENTION

This invention relates in general to apparatus for electrically inducing ejaculation of animals. More specifically, it relates to a probe that has a self-contained circuitry for automatically generating an output signal waveform of alternating periods of stimulation and rest periods and of varying frequency during each stimulation period across a set of electrodes mounted on the probe.

It is well known that a proper electrical stimulus applied to an animal with a rectal probe will induce ejaculation. Recent studies have demonstrated that electroejaculation is an effective method for producing semen samples of good quality. Such samples are particularly useful in assessing the value of livestock such as bulls and rams for breeding purposes.

In early experiments, a standard 60 cycle household current, suitably reduced in voltage, powered a totally conductive probe. The circuit was completed through a needle electrode inserted in the thigh muscle. Conventional probes in current use are formed of an insulating material and carry multiple external electrodes. The electrical signal is applied across a pair of electrodes typically formed either as closed rings or as longitudinally extending metallic strips or bars.

One problem common to such probes has been that variations in the electrical resistance among individual animals, due for example to the presence of a layer of fecal material between the electrodes and the animal tissue, will cause substantial variations in the power level necessary to induce ejaculation. Unpredictable variations in the required power level occur even when the electrodes are mounted to project above the exterior surface of the probe and thereby displace the fecal layer. As a result, the output signal of conventional commercial electroejaculation devices are controlled manually to achieve ejaculation without injuring the animal by applying excessive power levels. At least a modest degree of skill is required in operating the device.

Another problem common to these probes is that the signal also stimulates motor nerve centers causing uncontrolled kicking, muscle spasms, or discomfort. This problem obviously increases the difficulty of obtaining samples and increases the danger of injury to both the animal and the operator.

The strength and form of the stimulation signal also influence on the effectiveness of the apparatus. While conventional electroejaculation apparatus employ output signals characterized by a wide variety of voltages, currents, frequencies and waveforms (typically a sinusoidal, 60 cycle signal with alternating periods of stimulation and rest), they have operated at a single, fixed frequency, or one of a limited number of fixed frequencies that is selected prior to operation. For example, a study by Watson reported in the *Australian Veterinary Journal,* Volume 40 (April, 1964) entitled "Field Collection and Evaluation of Semen from Bulls Using Electroejaculation" employed apparatus with a maximum output of 20 volts at 0.5 ampere applied at a frequency of 20 cps. In a more recent article by Furman, Ball and Seidel entitled "Electroejaculation of Bulls Using Pulse Waves of Variable Frequency and Length" appearing in the *Journal of Animal Science,* Volume 40, No. 4 (1975), sinusoidal stimulation at a frequency of 50 or 80 cps was found to be significantly more effective than the same stimulation at 20 cps. In general, a single frequency may be effective for one species of animals and relatively ineffective for others. Further the response of animals within one species to a selected frequency may vary significantly.

Another difficulty with conventional electroejaculation apparatus is that they require a relatively heavy, cumbersome electrical unit to generate the output signal. For example, the commercially available circuitry used in the Furman experiment (manufactured by the Nicholson Manufacturing Co., a subsidiary of the assignee of the present application) weighs approximately 35 pounds.

This system suffers for several other disadvantages characteristic of conventional electroejaculation apparatus. First, the circuitry has a set of manual controls to select a general power level and to vary manually the voltage output within that level. Manual operation is relatively slow and requires a skilled operator to achieve consistently good results without injury to the animal. Such systems are also susceptible to malfunction due to contamination of the circuitry by dirt, dust and water. In particular, short circuits are a recurring problem since the probe is typically immersed in a conductive solution prior to use.

It is therefore a principal object of this invention to provide an electroejaculation device that is convenient to use and is highly effective for a variety of animals including common livestock and exotic animals.

Another object is to provide an electroejaculation device that is lightweight, compact, fully automatic and induces ejaculation in a significantly shorter time period than conventional apparatus.

Yet another object is to provide an electroejaculation device that is safe for both the animal and the operator.

Still another object of the invention is to provide an electroejaculation device that is resistant to malfunction caused by contaminants.

A further object is to provide an electroejaculation device that has a relatively low power consumption and can be powered by a standard automobile battery.

A still further object of this invention is to provide an electroejaculation device with the foregoing advantages that has a significantly lower cost of manufacture than conventional apparatus of this type.

SUMMARY OF THE INVENTION

An electronic circuit that generates an electrical stimulation signal is enclosed within an insulating housing forming a rectal probe. The signal is applied to a set of electrodes, preferably longitudinally extending rods angularly displaced from one another by an acute angle, mounted on the exterior of the housing. The circuit automatically generates an output waveform of alternating stimulation and rest periods in which the total energy of the signal during the stimulation periods increases automatically for successive stimulation periods and the frequency of the signal during at least part of each stimulation period varies over a preselected range of frequencies.

In a preferred form, the circuit includes elements for generating two synchronized sequences of ramp signals, a voltage controlled oscillator responsive to the sequences of ramp signals, and circuitry for amplifying the output of the oscillator. Preferably the circuit automatically repeats the cycle of operation and protects the circuit against an improper connection to a DC power supply.

The circuit and an electrical connector between the circuit and an external power source are preferably hermetically sealed within the probe. Also, the connector is preferably adapted to direct the output signal to a second rectal probe that does not have a self-contained signal generating circuit.

These and other objects and features of the invention will be more fully understood from the following detailed description which should be read in light of the accompanying drawings.

DETAILED DESCRIPTION OF THE ILLUSTRATED EMBODIMENTS

Figure 1:
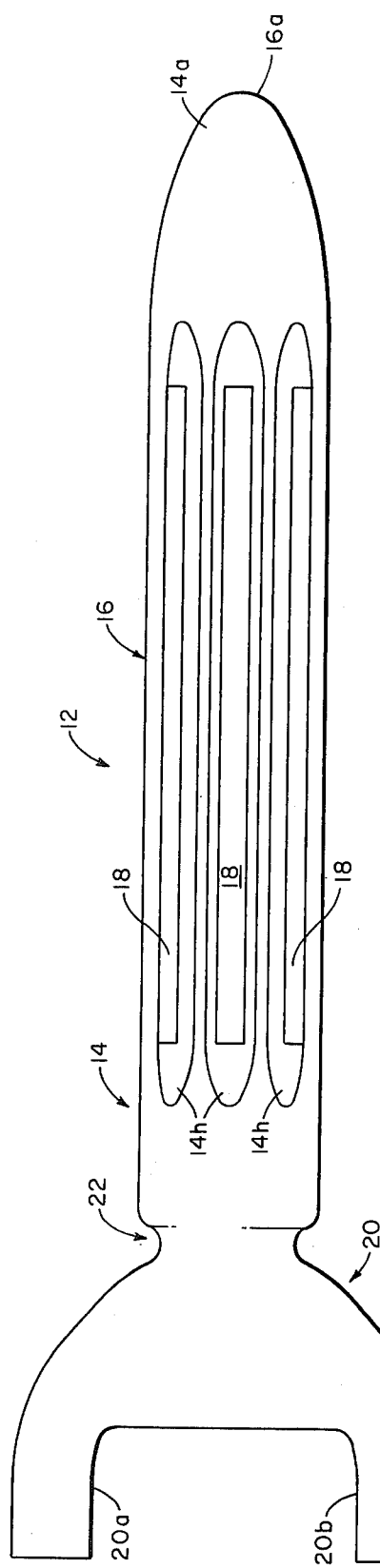
FIG. 1 is a top plan view of an electroejaculation device according to the invention.
Figure 2:
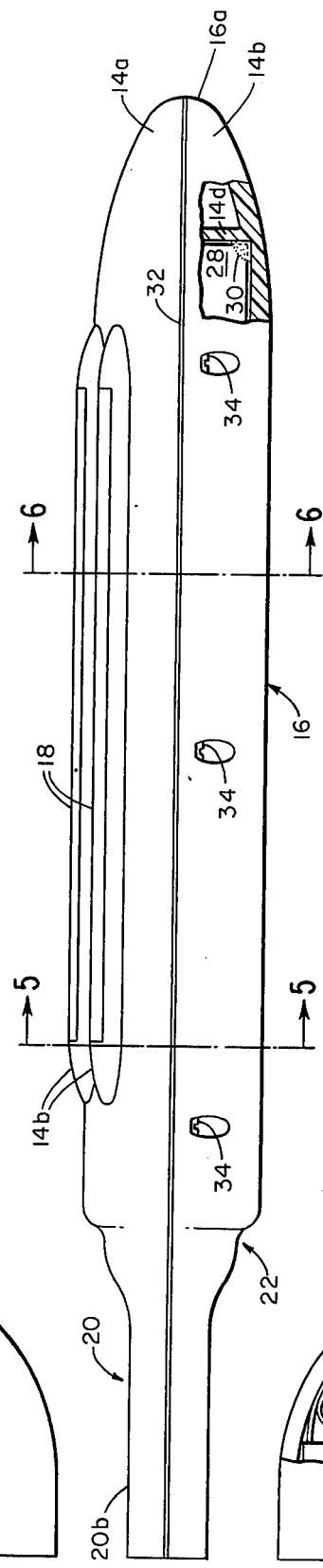
FIG. 2 is a view in side elevation of the device shown in FIG. 1 with a housing portion broken away.
Figure 3:
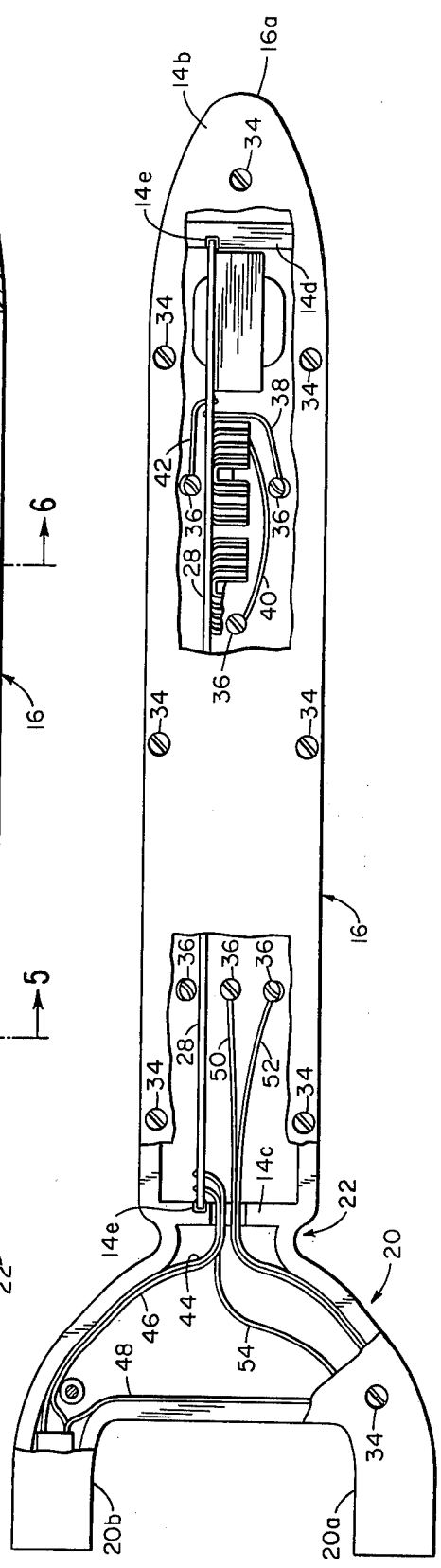
FIG. 3 is a bottom plan view of the device shown in FIGS. 1 and 2 with housing portions broken away.

FIGS. 1-6 show an automatic electroejaculation device 12 according to the invention having a housing 14 formed in two parts, an upper half 14a and a lower half 14b that mate at their peripheries. The housing has a generally cylindrical portion 16, that together with a set of electrodes 18 form a rectal probe, and a generally Y-shaped handle portion 20 connected to one end of the probe portion 16 by a region 22 of reduced diameter. The handle portion 20 has two branches 20a and 20b that each hold a plug 24 that provides an electrical connection between an external power source 26 (FIG. 8) such as a standard 12 volt battery and a printed circuit (PC) board 28.

The probe portion 16 of the housing 14 is adapted for insertion in the anal cavity of an animal. A rounded nose portion 16a facilitates the insertion and the narrowed region 22 is adapted to be gripped by the sphincter muscles. The region 22 reduces the likelihood that the probe will be expelled, automatically locates the probe, and relaxes the animal. The length and diameter of the probe portion 16 will vary from species to species, and may vary among animals with a single species.

Figure 4:
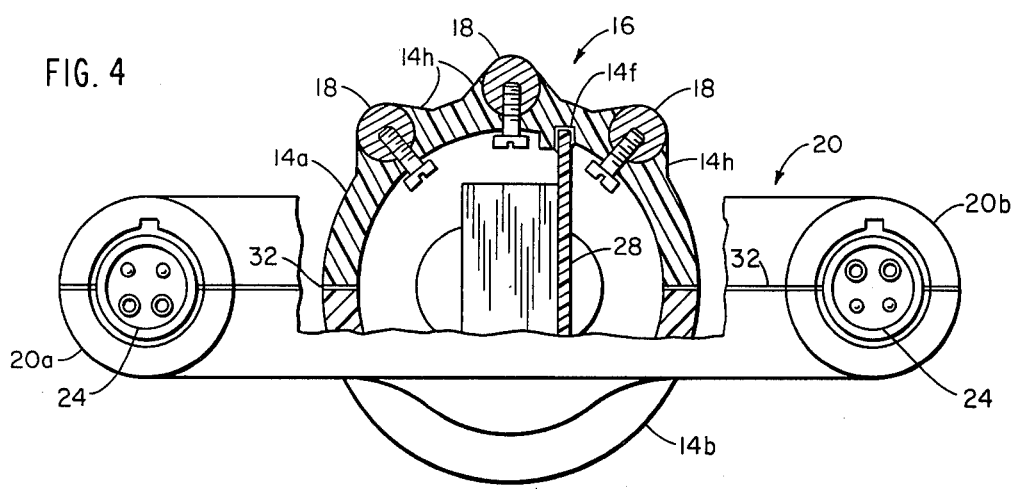
FIG. 4 is an end view in partial section of the device shown in FIGS. 1-3.
Figure 5:
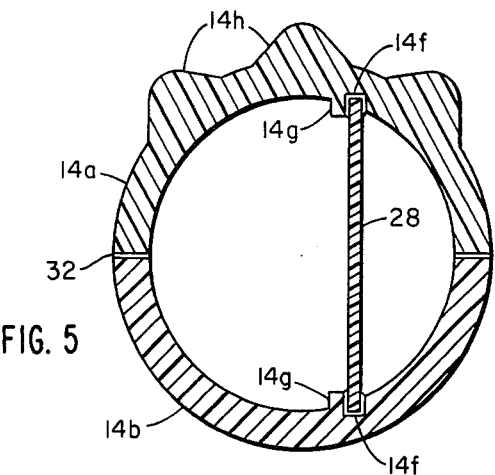
FIGS. 5 and 6 are views in vertical section taken along the lines 5—5 and 6—6, respectively, in FIG. 2.
Figure 6:
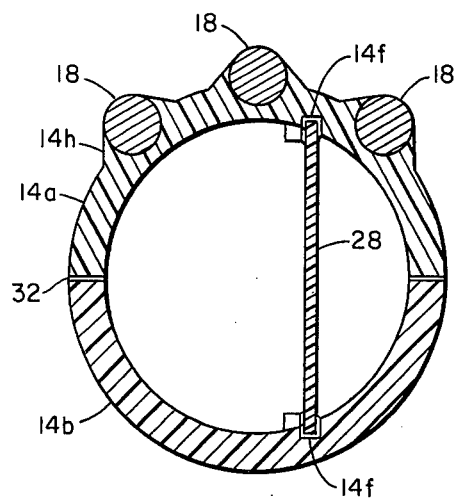

The housing halves 14a and 14b are generally hollow with transverse walls 14c and 14d positioned near the region 22 and the nose 16a, respectively. As can be best seen in FIG. 3, the support walls 14c and 14d each have a groove 14e that engages an end of the PC board 28. In addition, as is best seen in FIGS. 4-6, each housing half 14a and 14b has a longitudinally extending groove 14f and an adjoining rib 14g formed on its inner surface that engage the sides of the PC board 28. An adhesive 30, preferably a silicone rubber cement, secures the corners of the PC board to the housing.

The housing 14 is formed of a rigid insulating material such as a thermosetting plastic. Preferably the halves 14a and 14b are formed of the plastic sold by the General Electric Co. under the trade designation Noryl FN 215 by standard injection molding techniques. When the PC board and other components described hereinbelow are secured to the housing halves, they are sealed together with a suitable adhesive such as a two part sealant manufactured by Loctite Corporation under the trade designations "Locquic Primer, Grade N" and "Gasket Eliminator 515 Sealant." This material forms an adhesive layer 32 around the entire mating edges of the halves 14a and 14b as well as bonding the housing halves to the plugs 24. The halves are also secured in the assembled state by screws 34 that thread into the housing half 14a. Thus joined, the housing 14 is hermetically sealed. This seal prevents a malfunction of the device due to contaminants such as dirt, dust or water reaching the PC board or any of the electrical connection within the probe or the handle.

A set of electrode mounts 14h are integrally formed on the upper housing half 14a. Each mount 14h holds an electrode 18 so that a substantial portion of the side of each electrode is exposed and directed radially away from the device. The mounts also place the electrodes in a "raised" position with respect to the housing which together with the orientation of the exposed electrode surface promotes a good electrical contact between the electrodes and the animal tissue. The raised electrodes are particularly effective in displacing the layer of fecal material that usually lines the intestinal walls. The improved electrical connection afforded by the electrodes 18 and the mounts 14h reduces the internal electrical resistance and thereby lowers the power levels required to produce ejaculation. This also reduces the likelihood that the animal will be injured by an application of a signal that is strong enough to burn tissue.

Figure 7:
FIG. 7 is an enlarged plan view of an electrode shown in FIGS. 1, 2, 4 and 6.

The electrodes 18 (FIG. 7) are preferably formed from stainless steel rods which are drilled and tapped to receive mounting screws 36. The use of standard rod stock significantly reduces the manufacturing costs of fabricating the electrodes. It should also be noted that the leading and trailing ends of the mounts 14h are tapered to facilitate the insertion and removal of the probe.

The electrodes are electrically connected to the PC board by wires 38, 40 and 42. The "outer" electrodes are connected directly to one another. The output signal of the circuit is applied between one of the outer electrodes and the "middle" electrode. Because the electrodes are in parallel alignment with the angular displacement between the electrodes an acute angle, preferably forty degrees, the electrical stimulus to the animal between adjacent electrodes produces a minimal stimulation of the nerve centers controlling motor functions. As a result, involuntary physical activity such as kicking with the hind legs, arching of the back, and the discomfort or pain of other muscle contractions is minimized.

The housing 14 also encloses wires 44, 46, 48, 50, 52 and 54 that connect the PC board to the plugs 24. The wires 44 and 46 connect the external power source through the plug 24 in the branch 20a to the PC board. The wire 48 is connected directly between the plugs 24. The wires 50 and 52 are connected at one end to a pair of the electrodes 18 and at the other end to sockets on the plug 24 in the arm 20b. The wire 54 connects the ground wire 44 and the ground connection of the PC board to the plug 24 in the arm 20b.

Figure 8:
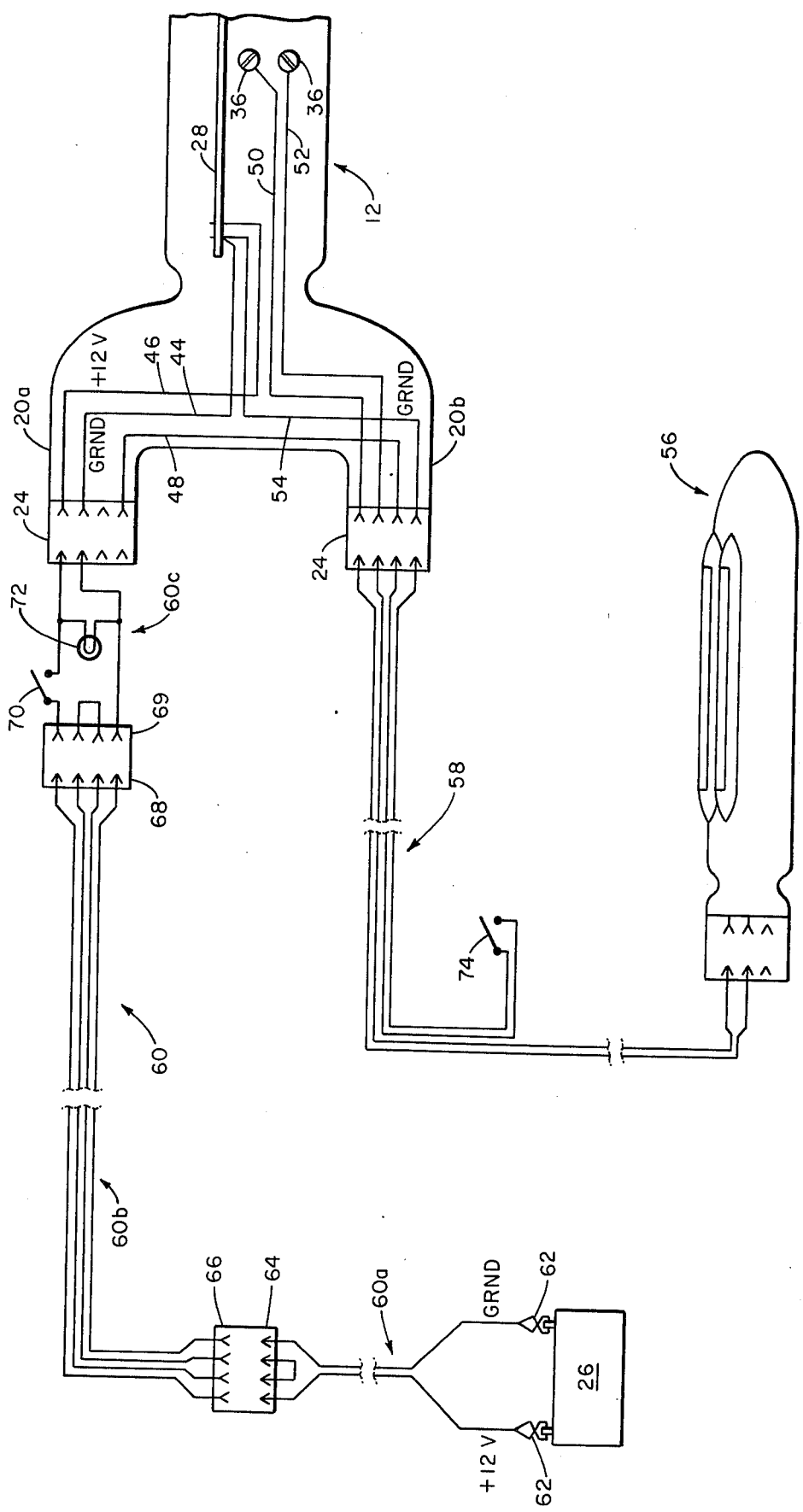
FIG. 8 is a schematic view of the device shown in FIGS. 1-6 connected between a battery and a second probe of smaller size.

With reference to FIG. 8, this wiring scheme allows the device 12 containing the signal generating PC board 28 to drive a secondary or auxiliary probe 56 that is connected by a cable 58 to the plug 24 in the branch 20b. A single device 12 can thus operate other probes of varying size which do not have self-contained signal generating circuits. The auxiliary probes can be larger or smaller than the device 12 depending on the nature of the animal. With a smaller probe 56, this invention has been successfully used on rams and exotic animals such as oryx and cheetahs.

With further reference to FIG. 8, a power cable 60 connects the external power source 26, preferably a standard 12 volt automobile or truck battery, to the plug 24 in the arm 20a. The cable 60 is divided into three sections 60a, 60b and 60c. Alligator clips 62, 62 connect section 60a to the terminals of the battery 26. A jack 64 and a plug 66 connect the sections 60a and 60b. A jack 68 and a plug 69 connect the sections 60b and 60c. The section 60c has a manually operated power control switch 70. When the switch 70 is closed, power is applied to the PC board circuit. A pilot light 72 indicates whether or not the device 12 is energized.

The cable 58 also has a manual switch 74 that is connected in series with the wires 48 and 54 to control the supply of power to the second probe 56. It should be noted that the switches 70 and 74 can be used together to provide two control points, or when the secondary probe 56 is used, the switch 70 can be removed entirely by connecting the jack 68 directly to the plug 24 in the arm 20a. In this latter situation, the wiring arrangement of the device 12 and the cables 58 and 60 is such that the switch 74 controls the supply of power to the PC board circuit.

Figure 9:
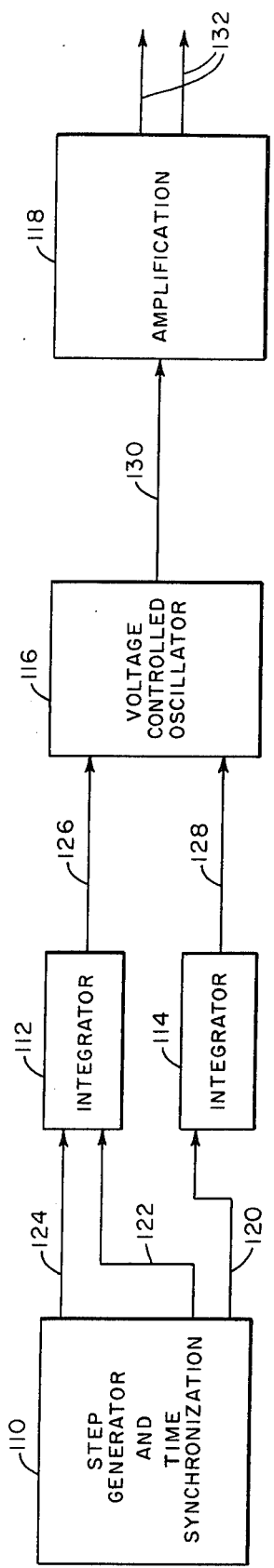
FIG. 9 is an electrical block diagram of the preferred circuit according to the invention.

Referring to FIG. 9, a preferred circuit for automatically generating a sequence of alternating stimulation periods and rest periods across electrodes 18, according to the invention, comprises, a step generator and time synchronization circuitry 110, a resettable integrating amplifier 112, a resettable, internally set, integrating amplifier 114, a voltage controlled oscillator 116, and an amplification circuit 118.

The timing for the entire system is controlled by a clock which, in this embodiment, is contained within the generator and synchronization circuitry 110. The clock period may be preset to any convenient value. In this preferred embodiment, for reasons which will become clear later, the clock is set to a frequency corresponding to a period equal to one-eighth of the time duration between the start of successive stimulation periods.

Figure 10:
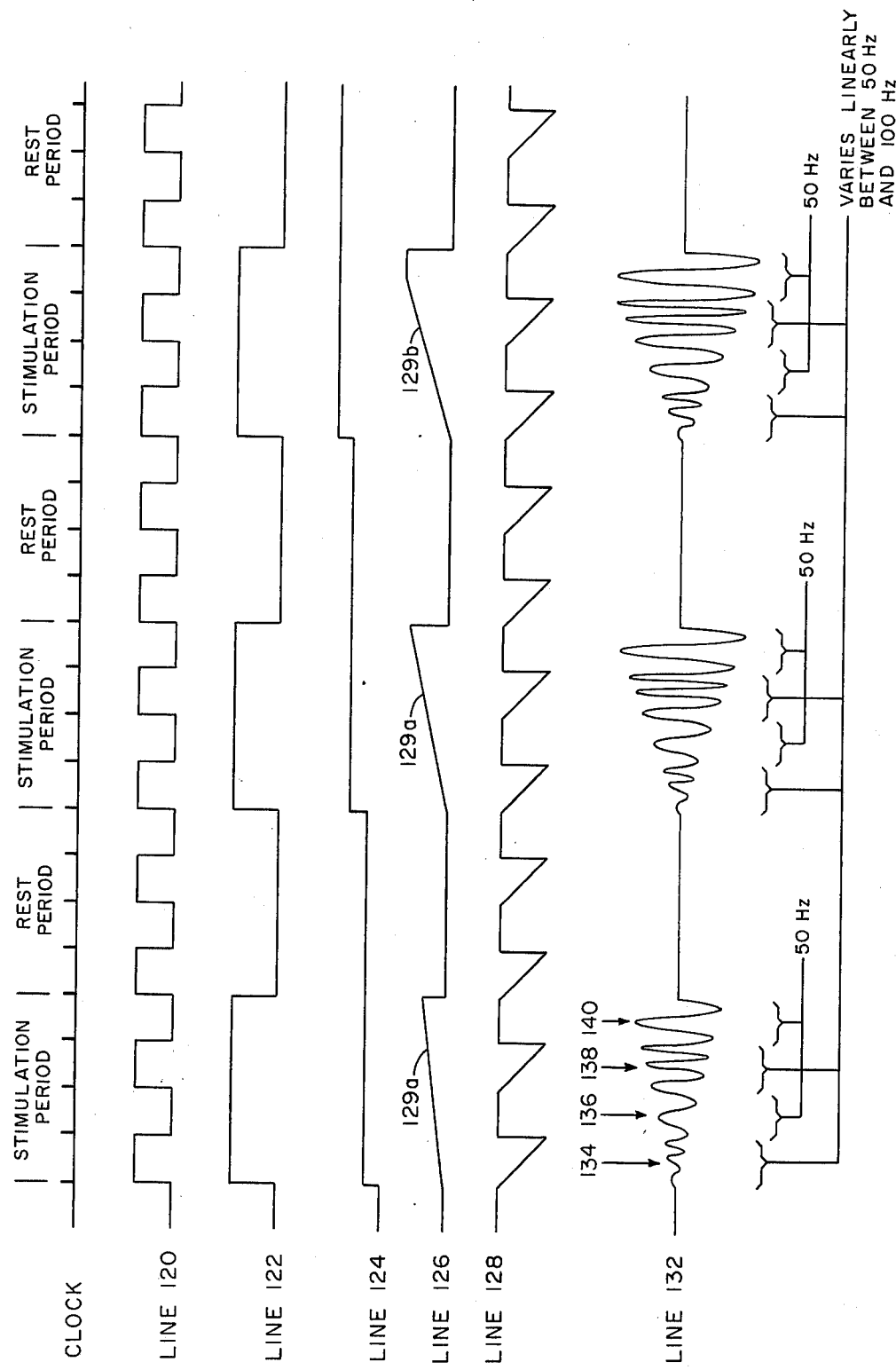
FIG. 10 is a graph versus time of several representative signal waveforms of the preferred circuit according to the invention.

Circuitry 110 provides three separate, synchronized output signals over lines 120, 122 and 124 (FIG. 10). The signal output over line 120 is a periodic signal, preferably a square wave, having a time period equal to twice the time duration between clock pulses (or a fundamental frequency equal to one-half the clock frequency). The signal output over line 122 is a periodic signal, also preferably a square wave, having a time period equal to eight times the time duration between clock pulses (or a fundamental frequency equal to one-eighth the clock frequency).

The signal output over line 124 is a stepped voltage signal synchronized to the signal on line 122 and the time duration of each step is equal to the repetition period of the signal over line 122. The magnitude of the voltage steps is preferably monotonically increasing but may be either constant (equal voltage increments) or any desired non-linear sequence. In the preferred embodiment, the magnitude of the voltage steps follows an exponential function, i.e., the magnitudes start with relatively small voltage steps or changes, and end with larger steps or changes, the sequence of voltage step differences following a substantially exponential curve of the form a $e^{t/\tau}$ there a and $\tau$ are constants.

Integrating amplifiers 112 and 114 provide a sequence of ramp output signals over lines 126 and 128, respectively (FIG. 10). The output signal over line 126 is derived by integrating the voltage signal level on line 124. Since that voltage level is synchronous with the signal over line 122, and since the output signal of the amplifier 112 is periodically reset to ground level when the signal level on line 122 goes to a ground level, the input signal on line 124 will be a constant value during the integration time. As a result, the output signal will be a sequence of sawtooth signals. In a particularly preferred embodiment, the integrated amplifier is operated so that it will saturate before the end of the integration period for input signals greater than a predetermined value. Hence, in the preferred embodiment, the sawtooth signals are clipped or saturated to provide the later stimulation periods with a total energy content greater than they might otherwise contain. Thus, in the preferred embodiment, the output saw tooth signals corresponding to the beginning of an operating cycle will be ramp signals 129a (FIG. 10) while those ramp signals 129b later in the cycle will be saturated at a predetermined output voltage. In any case, however, the slope of the initial ramp portion of each successive sawtooth signal will increase and the duration of all sawtooth signals will be constant.

Integrating amplifier 114 has a fixed internally set voltage level which is integrated during the integration time. The output of amplifier 114 returns or is reset to and is held at a positive potential (integration is toward ground level) whenever the signal level on line 120 is at a positive potential. This determines the integration time. The result is a saw tooth waveform on line 128 wherein each ramp has the same slope (set by the internal voltage) and time duration.

Thus, the integration time for integrating amplifier 112, 114 is determined by the signal levels on lines 122, 120, respectively. When the signal on line 122 is high (or floating) and the signal on line 120 is low (or ground), the respective integrating amplifier is enabled to integrate the input voltage signal. When the signal on line 122 is low or at ground and the signal on line 120 is high, the respective integrator is reset and the output is held substantially constant. Typical waveforms are illustrated in FIG. 10.

The voltage controlled oscillator 116 provides a sinusoidal output voltage signal over a line 130 whose instantaneous frequency is determined by the voltage level of the signal on line 128 and whose peak-to-peak amplitude is determined by the voltage level of the signal on line 126. In the preferred embodiment of the invention, the signal voltage levels are chosen so that the frequency output from the oscillator 116 varies between about 50 and 100 Hz. Amplification circuit 118 in combination with voltage controlled oscillator 116 provides an output signal to the electrodes over lines 132 having in this embodiment, a maximum amplitude of about 40 volts peak-to-peak at a maximum current of about 4 amperes. The maximum instantaneous power output is thus about 20 watts.

The signal output on lines 132 is diagrammatically depicted in FIG. 10. (For a stimulation period of one second, there would be many more cycles or pulses of the signal waveform than shown). In the output signal, the slew rate to saturation (if any) and hence the total energy for each succeeding stimulation period increases, and within each stimulation period, the instantaneous frequency varies. In the described embodiment, each stimulation period can be divided into four subperiods 134, 136, 138, 140 according to the instantaneous frequency pattern of the signal. In subperiods 134 and 138, the instantaneous frequency varies linearly from 50 to 100 Hz; and in subperiods 136 and 140 the instantaneous frequency is constant at 50 Hz. Other patterns of frequency variation could have been chosen.

Figure 11:
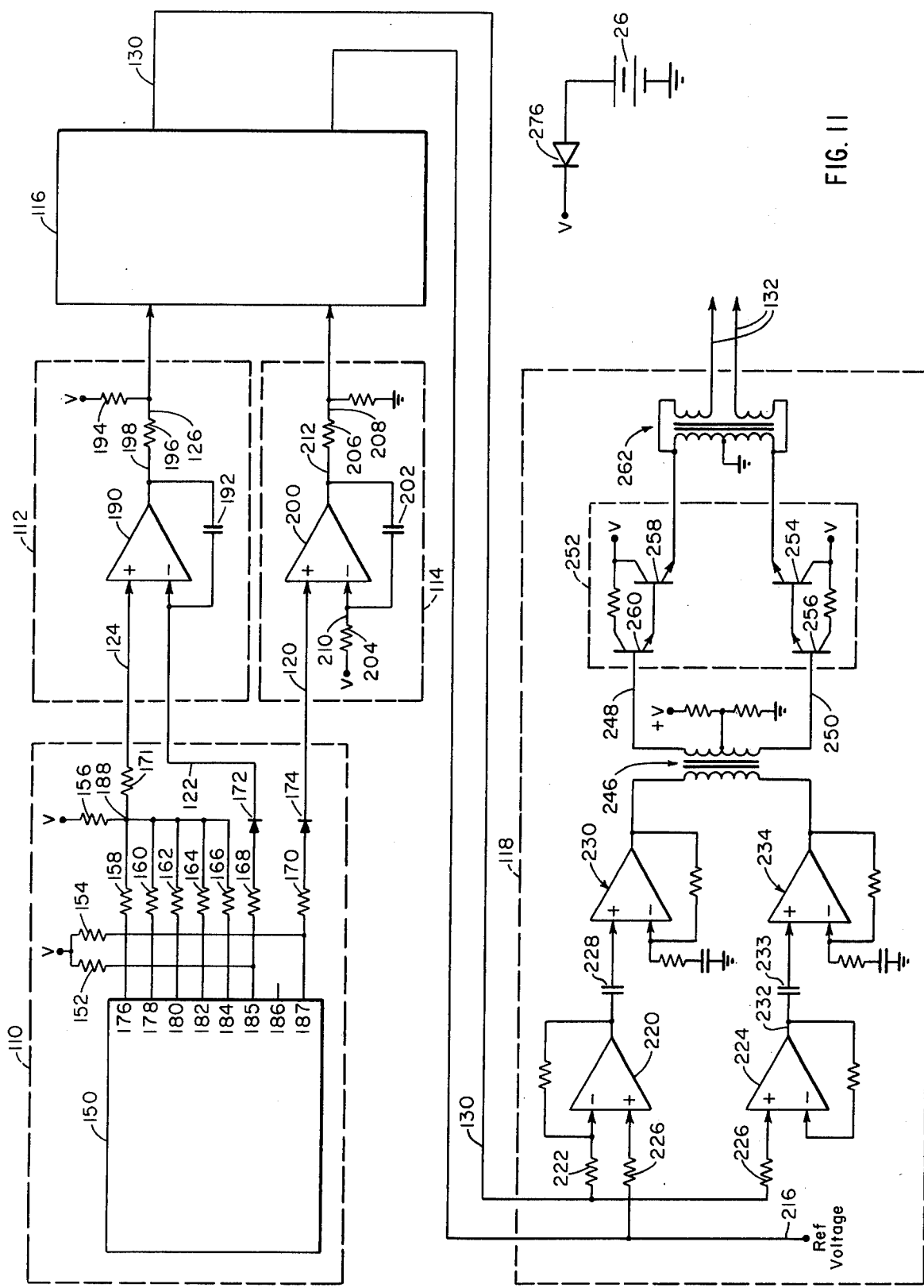
FIG. 11 is a more detailed electrical schematic circuit diagram of a preferred circuit according to the invention.

Referring now to the detailed electrical schematic circuit diagram of the preferred embodiment of the invention (FIG. 11), circuitry 110 comprises a programmed timer/counter 150, resistors 152, 154, 156, 158, 160, 162, 164, 166, 168, 170, 171, and diodes 172, 174. Timer/counter 150 which may be for example an integrated circuit type XR 2240, manufactured by Exar Integrated Systems, Inc., provides an eight bit binary output over lines 176, 178, 180, 182, 184, 185, 186, 187. Each output line corresponds to an open collector of a transistor. The transistor is either "off", in which case the output line is essentially floating or the transistor is "on" in which case the output line is at substantially a ground level.

Figure 12:
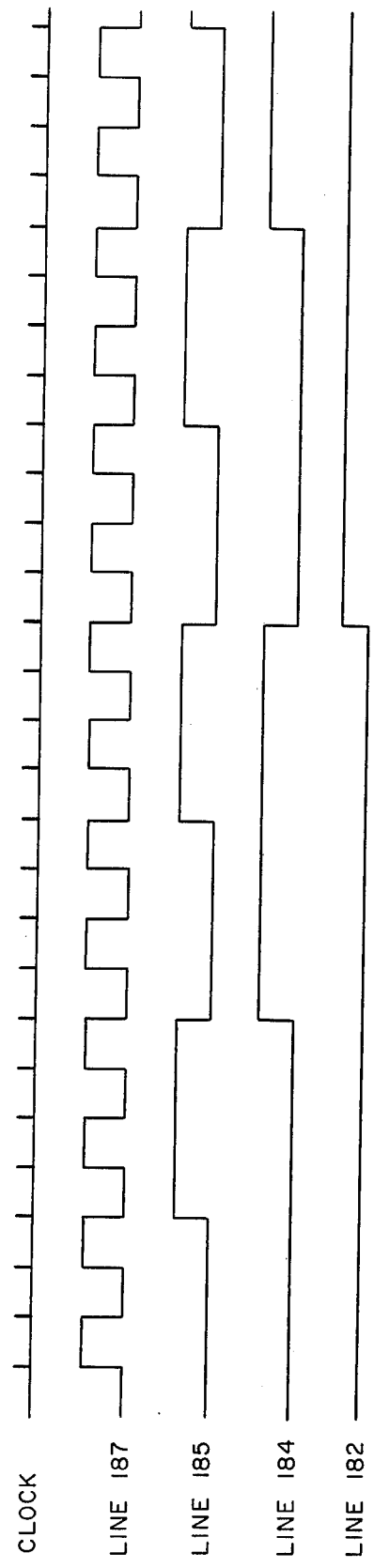
FIG. 12 is a graph versus time of several waveforms of said preferred circuit.

The timer/counter has an internal clock whose frequency is determined by an external RC circuit (not shown). The clock is set for a time period equal to one-eighth the period between stimulation pulses and hence if a stimulation pulse begins once every two seconds, the clock rate is set at 4 Hz. When power is applied to the circuitry, through the switch 70 or 74 (FIG. 8) the eight output lines are repeatedly and automatically sequenced from binary "0" wherein all lines are at ground level, to binary "127" wherein all lines are floating. The least significant output bit appears over line 187, corresponding to line 120 in FIG. 9. The most significant output bit appears over line 176. The output of line 186 is not used. For ease of explanation, the time between the beginning of successive stimulation periods shall be chosen to be two seconds. The corresponding output waveforms from timer/counter 150 for the four of the five least significant bits are shown in FIG. 12.

Outputs 176, 178, 180, 182, 184 are connected through resistors 158, 160, 162, 164, 166, respectively to a common point 188, which is connected to supply voltage through a resistor 156. Resistors 156, 158, 160, 162, 164, 166 are chosen to provide a predetermined sequence of voltage step levels over line 124 as the timer/counter sequences through the binary counts. Line 124 is connected to the positive input of an operational amplifier 190. As noted above, it is the voltage step waveform on line 124 which is the primary signal determining the amplitude envelope for the output sinusoidal signal over line 130. As the timer/counter 150 runs through its 128 states ($2^8$), there are provided thirty-two separate voltage level outputs over line 126 corresponding to the thirty-two different combinations of the five binary outputs over lines 176, 178, 180, 182, 184. These 32 voltage levels correspond to thirty-two different amplitude envelopes, one for each of the thirty-two stimulation periods during which power is applied to the electrodes.

While in the preferred circuit, the thirty-two stimulation periods continuously and automatically recycle, it would be simple for one skilled in digitial electronics to provide the logic necessary to terminate the binary counter and hence the stimulation pulses after the end of the thirtysecond stimulation period.

Resettable integrating amplifier 112 comprises operational amplifier 190, a capacitor 192, and resistors 194, 196. Operational amplifier 190 is connected in an integrating configuration using capacitor 192. The output of timer/counter 150 over line 185 is connected to the negative input of operational amplifier 190 through resistor 168 and diode 172. THus, the output of amplifier 190 is grounded during that time when the input over line 122 is at ground (the rest period) and is the integral of the voltage input over line 124 when the input to the amplifier over line 122 is high (the stimulation period). The resistors 156, 158, 160, 162, 164, 166 are chosen, in the preferred embodiment, so that the output of integrating amplifier 190 will saturate, before the end of the integration time, as the magnitude of the voltage steps increases. Consequently, the output of amplifier 190 over a line 198 is a sequence of saw tooth signals with each saw tooth having at least one initial ramp portion with a slope proportional to the voltage on line 124. The ramp portion flattens out (saturating) as the voltage reaches a predetermined level. Each saw tooth has a time duration of one second, and is separated from adjacent saw tooth signals by a ground level having a time duration equal in this embodiment to one second (FIG. 10). Thus the saw tooth output 198 of amplifier 190 during each stimulation period is a ramp signal (the integral of a constant input is a ramp) which may saturate before the end of the stimulation period, and which is returned to ground (and capacitor 192 is discharged) during each rest period. This signal is applied to the voltage controlled oscillator 116 through resistor 196, biased through resistor 194 to the supply voltage, to control the amplitude of the output signal from voltage controlled oscillator 116.

Resettable integrating amplifier 114 comprises an operational amplifier 200, a capacitor 202 and resistors 204, 206 and 208. Amplifier 200 is connected in an integrating configuration using capacitor 202. Its output signal controls the instantaneous frequency of the output from oscillator 116. The signal level applied to the positive input of amplifier 200 is derived from timer/counter 150 over line 187. This signal level is applied to input line 120 through resistor 170 and diode 174. The input to the negative terminal over a line 210 is provided from supply voltage through a resistor 204. The output of the amplifier 200 over line 212 is thus "gated" by the signal level on line 120. When the signal on line 187 is high, the output of amplifier 200 is high, at substantially supply voltage, (and the corresponding frequency output from voltage controlled oscillator 116 is, in the preferred embodiment, 50 Hertz). When the signal on line 187 is at ground level, amplifier 200 provides a negatively going ramp input to oscillator 116 through a resistor divider consisting resistors 206, 208. The output of oscillator 116 during this subperiod is a sinusoidal signal having a linearly varying instantaneous frequency, preferably varying from 50 Hz to 100 Hz.

The voltage controlled oscillator 116 may be for example Type XR 2206 manufactured by Exar Integrated Systems, Inc. This particular oscillator requires a reference voltage which is supplied to the device over a line 216. This reference voltage becomes the average value of the sinusoidal output signal over line 130.

The remainder of the circuitry is the amplification circuitry 118. The sinusoidal output of oscillator 116 is connected to an operational amplifier 220 through a resistor 222 and to a second operational amplifier 224 through a resistor 226. Amplifier 220 is connected as an inverting amplifier to invert the signal on line 130 about its average value. The output of inverting amplifier 22 is AC coupled through a capacitor 228 to, in the preferred embodiment, a buffer operational amplifier 230.

Operational amplifier 224 is connected to follow the input signal (line 130). Its output signal over a line 232 is substantially identical to its input signal and is AC coupled through a capacitor 233 to an operational amplifier 234. Operational amplifiers 190, 200, 220, and 224 are preferably part of a single integrated circuit Type LM3900 manufactured by National Semiconductor Co.

The operational amplifiers 230, 234, their inputs and hence their outputs being 180° out of phase, are connected to the primary of a transformer 246 in a push-pull configuration. The center tapped secondary of transformer 246 is connected over lines 248, 250, to a push-pull circuit 252. Push-pull circuit 252 may be of any type known in the art, and preferably comprises two Darlington circuits comprising transistors 254, 256, 258, 260. Circuit 252 drives a transformer 262 having a center tapped primary and configured preferably as shown in the drawing to provide, over lines 132, a forty volt peak to peak signal output at up to four amperes.

Operational amplifiers 230 and 234 may be contained on a single integrated circuit, preferably Type ULN-2278B manufactured by Sprague Electric Co.

Supply voltage is preferably provided to the automatic sequencing circuit through a protection means, diode 276, from the battery 26 of a truck, tractor, automobile or any other convenient 12 volt source. Diode 276 protects the circuit in case the battery is connected backwards.

Typical values for the resistors forming the voltage step waveform in the preferred embodiment are:
Resistor 158 — 1 kilohm
Resistor 160 — 7.2 kilohms
Resistor 162 — 4.5 kilohms
Resistor 164 — 8.2 kilohms
Resistor 166 — 20 kilohms
Resistor 188 — 5.6 kilohms Other embodiments of circuitry to provide a sequence of stimulation periods wherein the output signal has a varying instantaneous frequency for at least part of the stimulation period and wherein the total energy of the output signal for each succeeding period in the sequence is greater than the one that came before, will be obvious to those skilled in the art in light of the description above. Thus, for example, amplifiers 220 and 224 could be eliminated and their function incorporated into amplifiers 230, 234, respectively. Other modifications of the circuit, including circuit parameters, voltages, currents, and timing, will also occur to those skilled in the art.

To operate the device 12, the power cable 60 is connected to the terminals of a 12 volt DC power source. With the animal suitably restrained, the probe is inserted in the anal cavity. It is frequently helpful to first lubricate the probe with a soapy solution. The operator starts the device 12 by closing the switch 70. The device then automatically proceeds through its cycle of operation. The initial stimulation periods are at a low voltage to condition the animal to the probe. When the device is used on bulls, ejaculation is usually achieved when the operation cycle reaches the sixteenth or seventeenth stimulation period (out of thirty two periods in a complete cycle). When the ejaculation is completed, the operator opens the switch 70. If ejaculation is not reached after the completion of one cycle of operation, the circuit automatically repeats itself.

By way of illustration, but not of limitation, the device 12 adapted for use with bulls has an overall length of approximately 20 inches, a probe length of approximately 15 inches, and an outside probe diameter of approximately 2½ inches. Larger secondary probes for bulls have a probe length of approximately sixteen inches and an outer diameter of 3 inches. Smaller secondary probes suitable for use with rams have a probe length of approximately seven inches and an outer diameter of approximately one and one quarter inches. The electrodes for the standard bull size probe are approximately nine inches long and formed of three eighth inches diameter rod stock. When mounted, they are raised approximately three-eighths inch from the outer surface of the housing.

There has been described an electroejaculation device that is fully automatic, highly effective, convenient to use and safe for both the operator and the animal. It has a low weight, is powered by a readily-available, portable power source, and is relatively insensitive to contaminants such as dirt, dust and water. The device can be ready operated by a single person having a relatively low level of skill and achieve good results in at least half the time required with conventional manually operated units. Further, the device can be manufactured for at least half the cost of conventional units. In particular the housing is readily formed by standard injection molding techniques, the electrodes are readily fabricated, the electrical and electronic components are stock items, and assembly is relatively straightforward.

While the invention has been described with a circuit as being completely hermetically sealed within the housing, it will be understood that other techniques for assembling the housing are possible, albeit with an attendant increased likelihood of malfunctions. Further, alternative types of electrodes can be used, including bar electrodes that are more widely spaced from one another and conventional ring electrodes. In general, however, these other electrodes involve increased stimulation of muscle activity or require higher power levels. These and other variations and modifications will occur to those skilled in the art from the foregoing description and the accompanying drawings. Such modifications are intended to fall within the scope of the appended claims.

What is claimed and desired to be secured by Letters Patent is:

1. An automatic electroejaculation device for animals comprising
   A. a housing formed of a rigid insulating material having a hollow, generally cylindrical configuration,
   B. a plurality of electrodes mounted on the exterior of said housing, C. electronic circuit means for generating an output signal across said electrodes in an operating cycle of alternating stimulation periods and rest periods, where the total energy of said signal during the stimulation periods increases automatically for successive stimulation periods during said cycle and where the frequency of said signal varies automatically for at least part of each stimulation period, and D. means for establishing an electrical connection between said circuit means and an external power source.

2. An automatic electroejaculation device according to claim 1 wherein said circuit means comprises means to generate a first sequence of ramp signals, each ramp signal being substantially identical to each other ramp signal, and each ramp signal being separated from adjacent ramp signals by a predetermined time duration, means to generate a second sequence of sawtooth signals, each sawtooth signal having the same time duration, each sequential sawtooth signal having at least an initial ramp portion with a monotonically increasing magnitude of slope, and means responsive to said first and second sequences to generate said output signal, said first and second sequences being synchronized to each other.

3. The automatic electroejaculation device according to claim 2 wherein said responsive means comprises a voltage controlled oscillator responsive to said first and second sequences to provide an oscillating signal wherein the total energy of said oscillating signal during the stimulation periods increases automatically for successive stimulation periods during said cycle and where the frequency of said oscillating signal varies automatically for at least part of each stimulation period, and amplification circuitry means responsive to said oscillating signal to provide said output signal.

4. The automatic electroejaculation device of claim 3 wherein said second sequence generating means includes means for providing a stepped voltage output signal synchronized to said first sequence and means to selectively integrate said stepped voltage output signal to provide said second sequence of sawtooth signals.

5. The automatic electroejaculation device of claim 4 where said first sequence generating means includes means to periodically integrate a constant signal source input to provide said first sequence of ramp signals.

6. An automatic electroejaculation device for animals comprising

A. a housing formed of a rigid insulating material having a hollow, generally cylindrical configuration, B. a plurality of electrodes mounted on the exterior of said housing, C. electronic circuit means for generating an output signal across said electrodes in an operating cycle of alternating stimulation periods and rest periods, where the total energy of said signal during the stimulation periods increases automatically for successive stimulation periods during said cycle, and where said signal during said stimulation period alternates with a frequency of at least 50 Hz, D. means for establishing an electric connection between said circuit means and an external power source, and E. said electronic circuit means being mounted within said housing.

7. An automatic electroejaculation device according to claim 6 wherein said circuit means and said connection means are hermetically sealed within said housing.

8. An automatic electroejaculation device according to claim 6 wherein said circuit means includes means for automatically varying the frequency of said output signal for at least part of each stimulation period.

9. An automatic electroejaculation device according to claim 8 wherein said circuit means and said connection means are hermetically sealed within said housing.

10. An automatic electroejaculation device according to claim 9 wherein said circuit means comprises means to generate a first sequence of ramp signals, each ramp signal being substantially identical to each other ramp signal, and each ramp signal being separated from adjacent ramp signals by a predetermined time duration, means to generate a second sequence of sawtooth signals, each sawtooth signal having the same time duration, each sequential sawtooth signal having at least an initial ramp portion with a monotonically increasing magnitude of slope, and means responsive to said first and second sequences to generate said output signal, said first and second sequences being synchronized to each other.

11. The automatic electroejaculation device according to claim 10 wherein said responsive means comprises a voltage controlled oscillator responsive to said first and second sequences to provide an oscillating signal wherein the total energy of said oscillating signal during the stimulation periods increases automatically for successive stimulation periods during said cycle and where the frequency of said oscillating signal varies automatically for at least part of each stimulation period, and amplification circuitry means for amplifying said oscillating signal to provide said output signal.

12. The automatic electroejaculation device of claim 11 wherein said second sequence generating means includes means for providing a stepped voltage output signal synchronized to said first sequence and means to selectively integrate said stepped voltage output signal to provide said second sequence of sawtooth signals.

13. The automatic electroejaculation device of claim 12 where said first sequence generating means includes means to periodically integrate a constant signal source input to provide said first sequence of ramp signals.

14. An automatic electroejaculation device according to claim 9 wherein said circuit means includes means for protecting said circuit means against an improper connection to said external source.

15. An automatic electroejaculation device according to claim 9 wherein said circuit means includes means for automatically repeating said cycle.

16. An automatic electroejaculation device according to claim 9 wherein said electrodes are aligned along the longitudinal axis of said housing and are projected above the exterior surface of said housing to facilitate transmission of said signal to the animal.

17. An automatic electroejaculation device according to claim 6 wherein there are three electrodes angularly displaced from one another by approximately 40 degrees.

18. An automatic electroejaculation device according to claim 6 wherein said electrodes are stainless steel rods.

19. An automatic electroejaculation device according to claim 9 wherein said external power source is a 12 volt direct current battery and wherein said output signal has a maximum power of less than approximately 20 watts.

20. An automatic electroejaculation device according to claim 9 wherein said frequency during said part of said stimulation periods varies from 50 to 100 Hz.

21. An automatic electroejaculation device according to claim 6 further comprising
an auxiliary probe, and
cable means for electrically connecting said probe to said connection means, said connection means being operable to direct said output signal from said circuit means to said cable means.

* * * * *